(12) United States Patent
Krafft et al.

(10) Patent No.: US 8,258,350 B2
(45) Date of Patent: Sep. 4, 2012

(54) PROCESS FOR THE MANUFACTURE OF DICHLOROPROPANOL

(75) Inventors: Philippe Krafft, Rhode Saint Genese (BE); Patrick Gilbeau, Braine-le-Comte (BE)

(73) Assignee: Solvay (Societe Anonyme), Brussels (BE)

(*) Notice: Subject to any disclaimer, the term of this patent is extended or adjusted under 35 U.S.C. 154(b) by 599 days.

(21) Appl. No.: 12/529,777

(22) PCT Filed: Mar. 6, 2008

(86) PCT No.: PCT/EP2008/052711
§ 371 (c)(1), (2), (4) Date: Sep. 3, 2009

(87) PCT Pub. No.: WO2008/107468
PCT Pub. Date: Sep. 12, 2008

(65) Prior Publication Data
US 2010/0105862 A1  Apr. 29, 2010

Related U.S. Application Data

(60) Provisional application No. 61/013,680, filed on Dec. 14, 2007.

(30) Foreign Application Priority Data

Mar. 7, 2007 (FR) .................. 07 53689

(51) Int. Cl.
C07C 29/62 (2006.01)
C07C 31/36 (2006.01)
(52) U.S. Cl. .......... 568/844; 568/841; 568/852
(58) Field of Classification Search .......... 568/841, 568/844, 852
See application file for complete search history.

(56) References Cited

U.S. PATENT DOCUMENTS

| | | |
|---|---|---|
| 280,893 A | 7/1883 | Baujard |
| 865,727 A | 9/1907 | Queneau |
| 2,060,715 A | 11/1936 | Arvin |
| 2,063,891 A | 12/1936 | Dreyfus |
| 2,144,612 A | 1/1939 | Britton et al. |
| 2,198,600 A | 4/1940 | Britton et al. |
| 2,248,635 A | 7/1941 | Marple et al. |
| 2,319,876 A | 5/1943 | Moss |
| 2,444,333 A | 6/1948 | Castan |
| 2,505,735 A | 4/1950 | Halbedel |
| 2,726,072 A | 12/1955 | Herman |
| 2,811,227 A | 10/1957 | O'Connor |
| 2,829,124 A | 4/1958 | Napravnik et al. |
| 2,860,146 A | 11/1958 | Furman et al. |
| 2,876,217 A | 3/1959 | Paschall |
| 2,945,004 A | 7/1960 | Greenlee |
| 2,960,447 A | 11/1960 | Anderson et al. |
| 3,026,270 A | 3/1962 | Robinson, Jr. |
| 3,061,615 A | 10/1962 | Viriot et al. |
| 3,121,727 A | 2/1964 | Baliker et al. |
| 3,135,705 A | 6/1964 | Vandenberg |
| 3,158,580 A | 11/1964 | Vandenberg |
| 3,158,581 A | 11/1964 | Vandenberg |
| 3,247,227 A | 4/1966 | White |
| 3,260,059 A | 7/1966 | Rosenberg et al. |
| 3,341,491 A | 9/1967 | Robinson et al. |
| 3,355,511 A | 11/1967 | Schwarzer |
| 3,385,908 A | 5/1968 | Schwarzer |
| 3,445,197 A | 5/1969 | Resh et al. |
| 3,457,282 A | 7/1969 | Polak et al. |
| 3,618,295 A | 11/1971 | Geiger et al. |
| 3,711,388 A | 1/1973 | Gritzner |
| 3,766,221 A | 10/1973 | Becker |
| 3,839,169 A | 10/1974 | Moyer |
| 3,865,886 A | 2/1975 | Schindler et al. |
| 3,867,166 A | 2/1975 | Sullivan |
| 3,954,581 A | 5/1976 | Carlin |
| 3,968,178 A | 7/1976 | Obrecht et al. |
| 4,003,723 A | 1/1977 | Schafer et al. |
| 4,011,251 A | 3/1977 | Tjurin et al. |
| 4,024,301 A | 5/1977 | Witenhafer et al. |
| 4,127,594 A | 11/1978 | Anderson et al. |
| 4,173,710 A | 11/1979 | Boulet et al. |
| 4,197,399 A | 4/1980 | Noel et al. |
| 4,220,529 A | 9/1980 | Daude-Lagrave |
| 4,255,470 A | 3/1981 | Cohen et al. |
| 4,294,776 A | 10/1981 | Hardy et al. |

(Continued)

FOREIGN PATENT DOCUMENTS

CN  1296003 A  5/2001

(Continued)

OTHER PUBLICATIONS

Medium and Long-Term Opportunities and Risks of the Biotechnologial Production of Bulk Chemicals from Renewable Resources—The Potential of White Biotechnology—The BREW Project—Final Report—Prepared under the European Commission's GRXTH Programme (DG Research) Utrecht, Sep. 2006 (pp. 29-31).

(Continued)

Primary Examiner — Elvis O Price
(74) Attorney, Agent, or Firm — Beatrice C. Ortego

(57) ABSTRACT

Process for manufacturing dichloropropanol via reaction between glycerol and/or monochloropropanediol and a chlorinating agent in a reactor which is supplied with one or more liquid streams, in which the sum of the glycerol and monochloropropanediol contents in all the liquid streams introduced into the reactor is less than 50 wt % and in which all the liquid streams introduced into the reactor comprise at least one liquid recycling stream, the recycling stream forming at least 10 wt % of all the liquid streams introduced into the reactor.

10 Claims, 1 Drawing Sheet

U.S. PATENT DOCUMENTS

| | | | |
|---|---|---|---|
| 4,390,680 A | 6/1983 | Nelson | |
| 4,405,465 A | 9/1983 | Moore et al. | |
| 4,415,460 A | 11/1983 | Suciu et al. | |
| 4,464,517 A | 8/1984 | Makino et al. | |
| 4,499,255 A | 2/1985 | Wang et al. | |
| 4,595,469 A | 6/1986 | Foller | |
| 4,609,751 A | 9/1986 | Hajjar | |
| 4,634,784 A | 1/1987 | Nagato et al. | |
| 4,655,879 A | 4/1987 | Brockmann et al. | |
| 4,935,220 A | 6/1990 | Schneider et al. | |
| 4,960,953 A | 10/1990 | Jakobson et al. | |
| 4,973,763 A | 11/1990 | Jakobson et al. | |
| 4,990,695 A | 2/1991 | Buenemann et al. | |
| 5,041,688 A | 8/1991 | Jakobson et al. | |
| 5,200,163 A | 4/1993 | Henkelmann et al. | |
| 5,278,260 A | 1/1994 | Schaffner et al. | |
| 5,286,354 A | 2/1994 | Bard et al. | |
| 5,344,945 A | 9/1994 | Grunchard | |
| 5,359,094 A | 10/1994 | Teles et al. | |
| 5,393,428 A | 2/1995 | Dilla et al. | |
| 5,445,741 A | 8/1995 | Dilla et al. | |
| 5,478,472 A | 12/1995 | Dilla et al. | |
| 5,567,359 A | 10/1996 | Cassidy et al. | |
| 5,578,740 A | 11/1996 | Au et al. | |
| 5,679,839 A | 10/1997 | Armand et al. | |
| 5,710,350 A | 1/1998 | Jeromin et al. | |
| 5,731,476 A | 3/1998 | Shawl et al. | |
| 5,744,655 A | 4/1998 | Thomas et al. | |
| 5,779,915 A | 7/1998 | Becker et al. | |
| 5,908,946 A | 6/1999 | Stern et al. | |
| 5,993,974 A | 11/1999 | Fukushima et al. | |
| 6,024,839 A | 2/2000 | Schufeldt | |
| 6,142,458 A | 11/2000 | Howk | |
| 6,177,599 B1 | 1/2001 | Cowfer et al. | |
| 6,270,682 B1 | 8/2001 | Santen et al. | |
| 6,288,248 B1 | 9/2001 | Strebelle et al. | |
| 6,288,287 B2 | 9/2001 | Ueoka et al. | |
| 6,350,888 B1 | 2/2002 | Strebelle et al. | |
| 6,350,922 B1 | 2/2002 | Vosejpka et al. | |
| 6,521,794 B2 | 2/2003 | Hirota | |
| 6,719,957 B2 | 4/2004 | Brady, Jr. et al. | |
| 6,740,633 B2 | 5/2004 | Norenberg et al. | |
| 6,831,201 B2 | 12/2004 | Katsuura et al. | |
| 7,126,032 B1 | 10/2006 | Aiken | |
| 7,128,890 B2 | 10/2006 | Ollivier | |
| 7,584,629 B2 | 9/2009 | Sohn et al. | |
| 2001/0014763 A1 | 8/2001 | Ueoka et al. | |
| 2003/0209490 A1 | 11/2003 | Camp et al. | |
| 2004/0016411 A1 | 1/2004 | Joyce et al. | |
| 2004/0024244 A1 | 2/2004 | Walsdorff et al. | |
| 2004/0150123 A1 | 8/2004 | Strofer et al. | |
| 2004/0179987 A1 | 9/2004 | Oku et al. | |
| 2004/0232007 A1 | 11/2004 | Carson et al. | |
| 2005/0261509 A1 | 11/2005 | Delfort et al. | |
| 2006/0052272 A1 | 3/2006 | Meli et al. | |
| 2006/0079433 A1 | 4/2006 | Hecht et al. | |
| 2006/0123842 A1 | 6/2006 | Sohn et al. | |
| 2007/0112224 A1 | 5/2007 | Krafft et al. | |
| 2007/0293707 A1 | 12/2007 | Wolfert et al. | |
| 2008/0146753 A1 | 6/2008 | Woike et al. | |
| 2008/0214848 A1 | 9/2008 | Krafft et al. | |
| 2009/0022653 A1 | 1/2009 | Strebelle et al. | |
| 2009/0198041 A1 | 8/2009 | Krafft et al. | |
| 2010/0029959 A1 | 2/2010 | Fan et al. | |

FOREIGN PATENT DOCUMENTS

| | | |
|---|---|---|
| CN | 101041421 | 9/2007 |
| DE | 58396 C | 8/1891 |
| DE | 180668 C | 1/1906 |
| DE | 197308 C | 11/1906 |
| DE | 238341 C | 3/1908 |
| DE | 197309 C | 4/1908 |
| DE | 869 193 | 3/1953 |
| DE | 1041488 B | 10/1958 |
| DE | 1075103 B | 2/1960 |
| DE | 1226554 B | 10/1966 |
| DE | 2 241 393 | 2/1974 |
| DE | 25 21 813 | 12/1975 |
| DE | 3003819 A1 | 8/1981 |
| DE | 3243617 | 5/1984 |
| DE | 216471 A1 | 12/1984 |
| DE | 3721003 C1 | 12/1988 |
| DE | 43 02 306 | 8/1994 |
| DE | 10203914 C1 | 10/2003 |
| DE | 10254709 A1 | 6/2004 |
| EP | 0 296 341 | 12/1988 |
| EP | 0347618 A2 | 12/1989 |
| EP | 0358255 A1 | 3/1990 |
| EP | 0421379 A1 | 4/1991 |
| EP | 0 452 265 | 10/1991 |
| EP | 0518765 A1 | 12/1992 |
| EP | 0522382 A1 | 1/1993 |
| EP | 0535949 B1 | 4/1993 |
| EP | 0561441 A1 | 9/1993 |
| EP | 0563720 A1 | 10/1993 |
| EP | 0568389 A1 | 11/1993 |
| EP | 0582201 A2 | 2/1994 |
| EP | 0 618 170 | 10/1994 |
| EP | 0 916 624 | 5/1999 |
| EP | 0919551 A1 | 6/1999 |
| EP | 0 774 450 | 2/2000 |
| EP | 1059278 A2 | 12/2000 |
| EP | 1106237 A1 | 6/2001 |
| EP | 1153887 A2 | 11/2001 |
| EP | 1163946 A1 | 12/2001 |
| EP | 1298154 A1 | 4/2003 |
| EP | 1411027 A1 | 4/2004 |
| EP | 1752435 A1 | 2/2007 |
| EP | 1752436 A1 | 2/2007 |
| EP | 1760060 A1 | 3/2007 |
| EP | 1762556 A1 | 3/2007 |
| EP | 1770081 A1 | 4/2007 |
| EP | 1772446 A1 | 4/2007 |
| EP | 1775278 A1 | 4/2007 |
| EP | 2 085 364 | 8/2009 |
| FR | 1 306 231 | 10/1961 |
| FR | 1 417 388 | 10/1964 |
| FR | 1476073 A | 4/1967 |
| FR | 1 577 792 | 8/1968 |
| FR | 2151107 | 4/1973 |
| FR | 2180138 | 5/1973 |
| FR | 2 217 372 | 2/1974 |
| FR | 2565229 A1 | 12/1985 |
| FR | 2752242 A1 | 2/1998 |
| FR | 2862644 A1 | 5/2005 |
| FR | 2868419 A1 | 10/2005 |
| FR | 2869612 A1 | 11/2005 |
| FR | 2869613 A1 | 11/2005 |
| FR | 2872504 A1 | 1/2006 |
| FR | 2881732 A1 | 8/2006 |
| FR | 2885903 A1 | 11/2006 |
| FR | 2 912 743 | 8/2008 |
| FR | 2 913 683 | 9/2008 |
| FR | 2913683 A1 | 9/2008 |
| FR | 2 917 411 | 12/2008 |
| FR | 2918058 A1 | 1/2009 |
| FR | 2925045 A1 | 6/2009 |
| FR | 2929611 A1 | 10/2009 |
| FR | 2935699 A1 | 3/2010 |
| FR | 2935968 A1 | 3/2010 |
| GB | 14767 A | 0/1914 |
| GB | 406345 | 8/1932 |
| GB | 404938 A | 1/1934 |
| GB | 467481 A | 6/1937 |
| GB | 541357 A | 11/1941 |
| GB | 679536 A | 9/1952 |
| GB | 702143 A | 1/1954 |
| GB | 736641 A | 9/1955 |
| GB | 799567 A | 8/1958 |
| GB | 984446 A | 2/1965 |
| GB | 984633 A | 3/1965 |
| GB | 1083594 A | 9/1967 |
| GB | 1286893 A | 8/1972 |
| GB | 1387668 A | 3/1975 |
| GB | 1 493 538 | 4/1975 |
| GB | 1414976 A | 11/1975 |

| | | | |
|---|---|---|---|
| GB | 2173496 A | 10/1986 | |
| GB | 2336584 A | 10/1999 | |
| HU | 2002-003023 | 3/2004 | |
| JP | 3927230 B2 | 11/1939 | |
| JP | 50-062909 | 5/1975 | |
| JP | 51021635 B | 7/1976 | |
| JP | 55041858 A | 3/1980 | |
| JP | 5629572 | 3/1981 | |
| JP | 5699432 | 8/1981 | |
| JP | 61 112066 A | 5/1986 | |
| JP | 62242638 A | 10/1987 | |
| JP | 63195288 A | 8/1988 | |
| JP | 2-137704 | 5/1990 | |
| JP | 03014527 A | 1/1991 | |
| JP | 03223267 A | 10/1991 | |
| JP | 3223267 A | 10/1991 | |
| JP | 04089440 A | 3/1992 | |
| JP | 04-217637 | 8/1992 | |
| JP | 625196 B2 | 4/1994 | |
| JP | 06184024 A | 7/1994 | |
| JP | 6321852 A | 11/1994 | |
| JP | 859593 | 3/1996 | |
| JP | 09-299953 | 11/1997 | |
| JP | 10139700 A | 5/1998 | |
| JP | 1998218810 A | 8/1998 | |
| JP | 2001-037469 | 2/2001 | |
| JP | 2001-213827 A | 8/2001 | |
| JP | 2001-261308 | 9/2001 | |
| JP | 2001-1261581 A | 9/2001 | |
| JP | 2002-02033 A2 | 1/2002 | |
| JP | 20020038195 A | 2/2002 | |
| JP | 2002-363153 A | 12/2002 | |
| JP | 2003-89680 A | 3/2003 | |
| JP | 2003081891 A | 3/2003 | |
| JP | 2005007841 A2 | 1/2005 | |
| JP | 2005097177 A2 | 4/2005 | |
| JP | 2007-008898 | 1/2007 | |
| JP | 2009-263338 | 11/2009 | |
| KR | 900006513 | 11/1987 | |
| KR | 1019920003099 B1 | 4/1992 | |
| KR | 10-514819 B1 | 9/2005 | |
| PL | 136598 | 3/1986 | |
| PL | 162910 | 1/1994 | |
| SU | 123153 | 1/1959 | |
| SU | 1125226 | 11/1984 | |
| SU | 1159716 | 6/1985 | |
| SU | 1685969 | 10/1991 | |
| WO | WO 95/14639 | 6/1995 | |
| WO | WO 96/07617 | 3/1996 | |
| WO | WO 96/15980 | 5/1996 | |
| WO | WO 97/48667 | 12/1997 | |
| WO | WO 98/37024 | 8/1998 | |
| WO | WO 99/14208 | 3/1999 | |
| WO | WO 9932397 A1 | 7/1999 | |
| WO | WO 0186220 A2 | 11/2001 | |
| WO | WO 02/26672 A2 | 4/2002 | |
| WO | WO 03/064357 | 8/2003 | |
| WO | WO 2004/056758 | 7/2004 | |
| WO | WO 2005021476 A1 | 3/2005 | |
| WO | WO 2005054167 A1 | 6/2005 | |
| WO | WO 2005/097722 | 10/2005 | |
| WO | WO 2005/115954 | 12/2005 | |
| WO | WO 2005/116004 | 12/2005 | |
| WO | WO 2006020234 A1 | 2/2006 | |
| WO | WO 2006/100311 A2 | 9/2006 | |
| WO | WO 2006/100312 A2 | 9/2006 | |
| WO | WO 2006/100313 A2 | 9/2006 | |
| WO | WO 2006/100314 A1 | 9/2006 | |
| WO | WO 2006/100315 A2 | 9/2006 | |
| WO | WO 2006/100316 A1 | 9/2006 | |
| WO | WO 2006/100317 A1 | 9/2006 | |
| WO | WO 2006/100318 A2 | 9/2006 | |
| WO | WO 2006/100319 A1 | 9/2006 | |
| WO | WO 2006/100320 A2 | 9/2006 | |
| WO | WO 2006100311 A2 | 9/2006 | |
| WO | WO 2006100312 A2 | 9/2006 | |
| WO | WO 2006100313 A2 | 9/2006 | |
| WO | WO 2006100314 A1 | 9/2006 | |
| WO | WO 2006100315 A2 | 9/2006 | |
| WO | WO 2006100316 A1 | 9/2006 | |
| WO | WO 2006100317 A1 | 9/2006 | |
| WO | WO 2006100318 A2 | 9/2006 | |
| WO | WO 2006100319 A1 | 9/2006 | |
| WO | WO 2006100320 A2 | 9/2006 | |
| WO | WO 2006/106153 A2 | 10/2006 | |
| WO | WO 2006/106154 A1 | 10/2006 | |
| WO | WO 2006/106155 A2 | 10/2006 | |
| WO | WO 2006106153 A2 | 10/2006 | |
| WO | WO 2006106154 A1 | 10/2006 | |
| WO | WO 2006106155 A2 | 10/2006 | |
| WO | WO 2007/054505 A2 | 5/2007 | |
| WO | WO 2007054505 A2 | 5/2007 | |
| WO | WO2007/144335 | 12/2007 | |
| WO | WO 2007144335 A1 | 12/2007 | |
| WO | WO 2008/101866 | 8/2008 | |
| WO | WO2008/110588 | 9/2008 | |
| WO | WO2008/145729 | 12/2008 | |
| WO | WO 2008/147473 | 12/2008 | |
| WO | WO 2008/152043 | 12/2008 | |
| WO | WO 2008/152044 | 12/2008 | |
| WO | WO 2008/152045 | 12/2008 | |
| WO | WO 2009/000773 | 12/2008 | |
| WO | WO 2009/016149 A2 | 2/2009 | |
| WO | WO2009/043796 A1 | 4/2009 | |
| WO | WO 2009/077528 | 6/2009 | |
| WO | WO 2009/077528 A1 | 6/2009 | |
| WO | WO 2009/095429 A1 | 8/2009 | |
| WO | WO 2009/121853 | 10/2009 | |
| WO | WO2009/121853 A1 | 10/2009 | |
| WO | WO 2010/029039 | 3/2010 | |
| WO | WO 2010/029039 A1 | 3/2010 | |
| WO | WO 2010/029153 | 3/2010 | |
| WO | WO 2010/029153 A1 | 3/2010 | |
| WO | WO 2010/066660 | 6/2010 | |

OTHER PUBLICATIONS

Ullmann Encyl. Industr. Chem., $5^{th}$ Ed., vol. A6, (1988), pp. 401-477.

Polymer Science Dictionary, M.S.M., Elsevier Applied Chemistry, London and New York 1989, p. 86.

Perry's chemical Engineers' Handbook, Sixth Edition, Section 21, pp. 21-55.

E. Milchert et al., "Installation for the Recovery of Dichloropropanois and Epichlorohydrin from the Waste Water in Epichlorohydrin Production", Pol. J. Appl. Chem., vol. 41, p. 113-118 (1997).

Kleiboehmer W., et al, Solvay Werk Rheinberg: Integrlerte Prozesse Separlerte Abwasserbehandlungen—Gewaesserschutz, Wasser, Abwasser 200 (Wissenschaftlich-technische Mitteilungen des Instituts Zur Foerderung der Wasserguerte- und Wassermengenwirtschaft e; V;-2005 p. 81/-8/5., vol. 5.

Klaus Weissermel, et al., "Industrial Organic Chemistry," ($3^{rd}$ Completely Revised Edition); VCH 1997. p. 93-98.

Klaus Weissermel, et al., "Industrial Organic Chemistry," ($3^{rd}$ Completely Revised Edition); VCH 1997. p. 276-277.

Klaus Weissermel, et al., "Industrial Organic Chemistry," ($3^{rd}$ Completely Revised Edition); VCH 1997. p. 347-355.

Ying Ling Liu, "Epoxy Resins from Novel Monomers with a Bis-(9,10-dihydra-9-oxa-10-oxide-10-phosphaphenanthrene-10-yl-) Substituent," Journal of Polymer Science: Part A: Polymer Chemistry, vol. 40, 359-368 (2002).

Ying Ling Liu, "Phosphorous-Containing Epoxy Resins from a Novel Synthesis Route," Journal of Applied Polymer Science, vol. 83, 1697-1701 (2002).

M. Schellentrager, "Untersuchungen zur oxidation Entfarbung aus gewahlter Reaktivfarbstoffe: Analyse der Abbauprodukte misteels hochauflosender LC-MS", Dissertation, XP 0002548413 (Jan. 1, 2006) w/ English Abstract.

Herman A. Bruson, et al., "Thermal Decomposition of Glyceryl Carbonates," Journal of the American Chemical Society, vol. 74, Apr. 1952 pp. 2100-2101.

Perry's Chemical Engineers Handbook 7th Ed., 11th Section, 1997, pp. 11.1-11.118 (submitted into two parts).

Perry's Chemical Engineers Handbook 7th Ed., 13th Section, 1997, pp. 13.1-13.108.

Perry's Chemical Engineers Handbook 7th Ed., 15th Section, 1997, pp. 15.1-15.47.
Ullmann's Encyclopedia of Industrial Chemistry 5th Ed., vol. A23, 1993, pp. 635-636.
Ullmann's Encyclopedia of Industrial Chemistry 5th Ed., vol. A13, 1989, p. 289.
Ullmann's Encyclopedia of Industrial Chemistry 5th Ed., vol. A11, 1988, pp. 354-360.
Attached certified Application No. FR 06.05325 filed Jun. 14, 2006 by Solvay S.A.—priority document to EP2007/55742 published as WO 2007/144335 (attached herein) 17 pgs.
Attached certified Application No. FR 07.53863 filed Mar. 15, 2007 by Solvay S.A. and published as FR2913683, 19 pgs (attached herein)—priority document to EP2007/55742 published as WO2007/144335 29 pgs (attached herein).
Gibson, "The preparation, properties, and uses of glycerol derivatives, Part III. The Chlorohydrins", 1931, Chemistry and Industry, Chemical Society, pp. 949-975.
Carre et al, 1931, "La transformation des alcools polyatomiques en mono-et en polychlorhydrines au moyen du chlorure de thionyle", Bulletin De La Societe Chimique De France, Societe Francaise De Chimie. Paris—ISSN 0037-8968, vol. 49, No. 49, pp. 1150-1154.
Fauconner, 1888, "Preparation de l'epichlorhydrine", Bull. Soc. Chim. FR, No. 50, pp. 212-214 (with enclosed translation in English).
Ullmann's Encyclopedia of Industrial Chemistry, "Industrially important epoxides", 1987, Fifth Completely Revised Edition, vol. A9, pp. 539-540.
Bonner et al, "The composition of constant boiling hydrochloric acid at pressures of 50 to 1220 millimeters", 1930, Journal of American Chemical Society, vol. 52, pp. 633-635.
Muskof et al, "Epoxy Resins" in Ullmann's Encyclopedia of Industrial Chemistry, 1987, 5th Ed., vol. A9, pp. 547-563.
Novelli, A., "The preparation of mono- and dichlorohydrins of glycerol", 1930, Anales Farmacia Bioquimica, vol. 1, pp. 8-19 (with English abstract).
Derwent Publications, AN 109:6092 CA, JP 62-242638, Oct. 23, 1987, 1 pg.
Derwent Publications, AN 1987-338139 [48], JP 62-242638, Oct. 23, 1987, 1 pg.
I. Miyakawa et al, Nagoya Sangyo Kagaku Kenkyusho Kenkyu Hokoku, 10, 49-52 (1957). (Abstract in English only). 1 pg.
Han Xiu-Ying et al, Shanxi Daxue Xuebao Bianjibu, 2002, 25(4), 379-80. (Abstract in English only), 1 pg.
Semendyaeva et al, 1981. Khimicheskaya Promyshlennost, Seriya: Khomaya Promyshlennost, 5. 21-2 (CA Summary). XP 002465275, 1 pg.
Rudnenko, EV, et al., 1988, Lakokrasochnye Materially i 1kh Primenenie, 4 69-71 (CA Summary) XP 002465276, 1 pg.
Kirk-Othmer Encyclopedia of Chemical Technology, 1978, 3rd Ed., vol. 4, Blood, Coagulants and Anticoagulants to Cardiovascular Agents. p. 847-848.
Jeffrey Lutje Spelberg, et al, A Tandem Enzyme Reaction to Produce Optically Active Halohydrins, Epoxides and Diols, Tetrahedron: Asymmetry, Elsevler Science Publishers, vol. 10, No. 15, 1999, pp. 2863-2870.
Oleoline.com. Glycerine Market report, Sep. 10, 2003, No. 62, 31 pgs.
Notification Under Act. No. 100/2001, Coll. As Amended by Act No. 93/2004, Coll. To the extent of Annex No. 4 (SPOLEK) Nov. 30, 2004, 80 pgs.
Documentation Under Act. No. 100/2001 Coll. As Amended by Act. No. 93/2004 Coll in the scope of appendix No. 4 (SPOLEK) Jan. 11, 2005, 86 pgs.
K. Weissermel & H.J. Arpe, Industrial Organic Chemistry, Third, Completely Revised Edition, VCH, 1997, pp. 149 & 275.
Industrial Bioproducts: "Today and Tomorrow." Energetics, Inc. for the U.S. Department of Energy, Office of Energy Efficiency and Renewable Energy, Office of the Biomass Program, Jul. 2003, pp. 49, 52 to 56.
Kirk Othmer Encyclopedia of Chemical Technology, Fourth Edition, 1992, vol. 2, p. 156, John Wiley & Sons, Inc.
Ullmann's Encyclopedia of Industrial Chemistry, Fifth, Completely Revised Edition, 1988, vol. A13, pp. 292-293.

The Merck Index, Eleventh Edition, 1989, pp. 759-760.
Ullmann's Encyclopedia of Industrial Chemistry, Fifth completely Revised Edition, vol. A1, 1985, pp. 427-429.
Ullmann's Encyclopedia of Industrial Chemistry, Fifth Completely Revised Edition, vol. A6, 1986, pp. 240-252.
Hancock, E.G., Propylene and its Industrial Derivatives, 1973, pp. 298-332.
K. Weissermel & H.J. Arpe, Industrial Organic Chemistry, Third, Completely Revised Edition, VCH 1997, pp. 149-163.
K. Weissermel & H.J. Arpe, in Industrial Organic Chemistry, Third, Completely Revised Edition, VCH 1997, pp. 275-276.
Robert T. Morrison & Robert N. Boyd, Organic Chemistry, 5th Ed., vol. II, pp. 666 to 667 and 712 to 714 (Japanese Translation), published on Jul. 10, 1970, Tokyo Kagaku Dozin Co., Ltd. (and similar passages but retrieved from the English Fifth Edition of the Book, 1987).
Perry's Chemical Engineers' Handbook, Sixth Edition, Robert H. Perry, Don Green, 1984, Section 21-64 to 21-68.
Iwanami et al, Dictionary of Physics and Chemistry, Third Edition, Ryo Midorikawa /Iwanami Shoten, Publishers, May 29, 1971, pp. 270-271, 595 and 726.
Expert Opinion on the Environment Impact Assessment Documentation Pursuant to Annex No. 5 of Act No. 100/2001 Coll., as amended by later regulations of the project/intent combined process for the manufacture of epichlorohydrin (SPOLEK) Apr. 2005.
Kirk Othmer Encyclopedia of Chemical Technology, Third Edition, vol. 12, 1980, pp. 1002-1005.
Chemical Engineering Handbook, the 6th Edition, Edited by the Society of Chemical Engineers, published by Maruzen Co, Ltd., 1999, pp. 1296-1306 Pub. Feb. 25, 1999 w/English translation of p. 1296, Table 28.4, p. 1298, left column, lines 4-13 and p. 1305, Table 28.10.
Product Brochure of De Dietrich Company, Apr. 1996, pp. 3, 8 and 9 w/English translation of p. 8, left column, lines 1-4, p. 9.
The Journal of the American Chemical Society, vol. XLV, Jul.-Dec. 1923, pp. 2771-2772.
Berichte Der Deutschen Chemischen Gesellschaft, 1891, vol. 24, pp. 508-510.
Catalogue of Nittetu Chemical Engineering Ltd. (Published in Mar. 1994).
12093 Chemicals, The Chemical Daily Co., Ltd. (Published on Jan. 22, 1993) with attached English translation of relevant excerpts, 24 pgs.
Chemicals Guide, Chemical Daily Co., Ltd. (Published on Jun. 15, 1990) with attached English translation of relevant excerpts.
J.B. Conant, et al, "Glycerol a,y-dichlorohydrin", Organic Syntheses Coll., 1941, vol. 1, p. 292-294 (5 pp.).
Gilman H., Organic Synthesis, Section 1, pp. 234-235 (no date)—attached English translation only.
Industrial Chemical Encyclopedia 5, p. 457 (no date)—attached English translation only.
"Epoxy resins", p. 36-46, by Shangai Resin Plant, Shangai People's Press, 1971—attached English translation only.
Martinetti, R. et al. "Environnement Le Recyclage du l'eau" Industrie Textile, Ste Sippe Sarl, Metz, FR, No. 1300 (Jul. 1, 1998), ISSN: 0019-9176 (no English abstract available)—8 pp.
"Rainwater Harvesting and Utilization" (United Nations Environment Program) Mar. 2002; XP003003726; Internet Citation extracted online on Jan. 1, 2006: URL:http://www.unep.or.ip/letc/ Publication—4 pp.
Myszkowski, J. et al. "Removal of chlorinated organic impurities from hydrogen chloride"; English Chemical Abstract summary only of Polish Patent No. 136598 B2 (Mar. 31, 1986); XP002352444; 1 pp.
Myszkowski, J. et al. "Removal of organic compounds from gaseous hydrogen chloride by an absorption method" Chemia Stosowana (1986) vol. 30(4) p. 545-51; English Chemical Abstract Summary only; XP002352445; 1 pp.
Milchert, E. et al. "Recovering hydrogen chloride and organic chloro compounds from the reaction mixture in the chlorination of ethylene"; English Chemical Abstract Summary only of Polish Patent No. 162910 B1 (Jan. 31, 1994); XP002352443; 1 pp.

Laine, D.F. et al. "The destruction of organic pollutants under mild reaction conditions; A review" Michochemical Journal, vol. 85, No. 2, 2007 pp. 183-193; available online Aug. 17, 2006; 12 pp.

[Unknown Author], Kirk Othmer Encyclopedia of Chemical Technology—vol. 2, p. 156, John Wiley and Sons, 1992.

Ma Zengxin et al, "recovery of Polyglycerol from residues of Synthetic Glycerol" Riyong Huaxue Gongye, 1997, 4, 21023 (English Abstract only).

Sang Hee Lee et al "Direct preparation of Dichloropropanol (DCP) from Glycerol Using Heteropolyacid (HPA) Catalysts: A Catalyst Screen Study," Catalysis Communications (9), 2008, p. 1920-1923.

Production and Prospect of the World Natural Glycerol by Zhu Shiyong, Cereals and Oils, vol. 1, 1997, pp. 33-38 (No English Translation).

Vinnolit; Vinnolit receives EU grant for water recycling project: Press Release, 2008: http://www.vinnolit.de/vinnolit.nsf/id/EN_Vinnolit_receives_EU_grant_for_water_recycling_project_.

N.W. Ziels Journal of American Oil Chemists' Society, Nov. 1956, vol. 33, pp. 556-565.

Perry's Chemical Engineers Handbook, Sixth Edition. McGraw Hill Inc., (1984) Section 18.

Vol. 83: Unit Operations II of Ullmann's Encyclopedia of Industrial Chemistry, Fifth Completely Revised Edition, Published by VCH, 1988.

W. Giger et al., "14C/12C-Ratios in Organic Matter and Hydrocarbons Extracted from Dated Lake Sediments," Nuclear Instruments and Methods in Physics Research B5 (1984), 394-397. XP-002631954.

Jurgen O. Metzger, "Fats and Oils as Renewable Feedstock for Chemistry," Eur. J. Lipid Sci. Technol. (2009), 111, 865-875, XP-002631953.

Bruce M. Bell, "Glycerin as a Renewable Feedstock for Epichlorohydrin Production. The GTE Process," Clean-Soil, Air, Water, vol. 36, No. 6, (2008) pp. 657-661. XP-002631952.

RD 436093, Aug. 10, 2000.

Ullmann's Encyclopedia of Industrial Chemistry, 2005, "pH Measurement and Control", Wiley-VCH GmbH & Co. KGaA, Weinheim, 10.1002/14356007.e19_e01; pp. 1-31 (32 pgs).

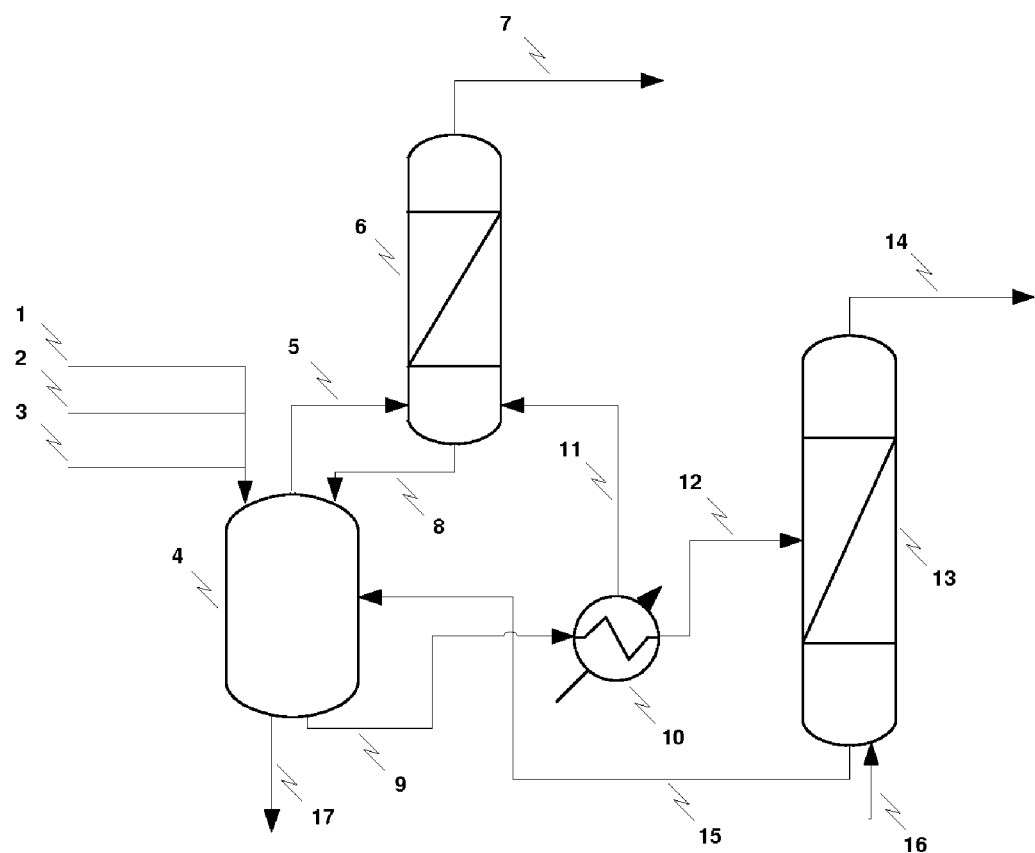

PROCESS FOR THE MANUFACTURE OF DICHLOROPROPANOL

CROSS-REFERENCE TO RELATED APPLICATIONS

The present patent application is a U.S. national stage application under 35 U.S.C. §371 of International Application No. PCT/EP2008/052771 filed Mar. 6, 2008, which claims the benefit of the French patent application No. FR 0753689 filed on Mar. 7, 2007, and of the provisional U.S. patent application No. 61/013,680 filed on Dec. 14, 2007, the content of each of these applications being incorporated herein by reference for all purposes.

The present invention relates to a process for manufacturing dichloropropanol. The present invention relates more specifically to a process for manufacturing dichloropropanol via reaction between glycerol and/or monochloropropanediol and a chlorinating agent.

Dichloropropanol is a reaction intermediate in the manufacture of epichlorohydrin and epoxy resins (*Kirk-Othmer Encyclopedia of Chemical Technology*, Fourth Edition, 1992, Vol. 2, page 156, John Wiley & Sons, Inc.).

According to known processes, dichloropropanol can be obtained in particular by hypochlorination of allyl chloride, by chlorination of allyl alcohol and by hydrochlorination of glycerol. The latter process exhibits the advantage that the dichloropropanol can be obtained starting from fossil raw materials or renewable raw materials and it is known that petrochemical natural resources, from which the fossil materials originate, for example oil, natural gas or coal, available on Earth are limited.

International Application WO 2005/021476 describes a process for manufacturing dichloropropanol via reaction between glycerol and/or monochloropropanediol and gaseous hydrogen chloride in the presence of acetic acid as a catalyst. The glycerol and/or monochloropropanediol content in the entirety of the liquid supply of the reactor is at least 50 wt %. The entirety of the supply comprises a recycling stream. In this process, undesirable products are formed and collected as residues in a tank.

The present invention aims to solve this problem by providing a novel process which limits the formation of undesirable by-products without however decreasing the selectivity of the reaction for dichloropropanol.

The invention hence relates to a process for manufacturing dichloropropanol via reaction between glycerol and/or monochloropropanediol and a chlorinating agent in a reactor which is supplied with one or more liquid streams, in which the sum of the glycerol and monochloropropanediol contents in all the liquid streams introduced into the reactor is less than 50 wt % and in which all the liquid streams introduced into the reactor comprise at least one liquid recycling stream, the recycling stream forming at least 10 wt % of all the liquid streams introduced into the reactor.

One of the main features of the present invention lies in the fact that the sum of the glycerol and monochloropropanediol contents in all the liquid streams that supply the glycerol chlorination reactor is less than 50 wt %. This makes it possible to reduce the amount of undesirable by-products. An additional advantage of this procedure is in tolerating a greater content of by-products in the reactor with, as a result, a concomitant decrease of the purge flow from the reactor and of the concentration of recoverable products in the purge flow, and therefore a reduction in the size of the installations for treating the purges. All these advantages contribute to a reduction in the overall cost of the process. Furthermore, this also makes it possible to reduce the reaction volume. As the reactions are balanced, it is thus possible to increase the rate of dichloropropanol synthesis by ensuring an effective removal of the latter from the reaction medium, in order to maintain a low concentration of dichloropropanol. This requires removing a large amount of the reaction medium, separating the dichloropropanol from the rest of the constituents of the reaction medium and recycling the rest of the reaction medium. These two joint operations, that is to say the removal of dichloropropanol and keeping a greater content of by-products in the reactor may be expressed by the glycerol and monochloropropanediol content of all the liquid streams that supply the glycerol chlorination reactor.

Another of the main features of the present invention lies in the fact all the liquid streams introduced into the reactor comprise at least one liquid recycling stream, the recycling stream forming at least 10 wt % of all the liquid streams introduced into the reactor. Such a recycling stream has several advantages. Firstly, it helps to lower the sum of the glycerol and monochloropropanediol contents in all the liquid streams that supply the glycerol chlorination reactor to less than 50 wt % without introducing external compounds and the need to recycle and dispose of such compounds. External compounds do not comprise the reactants used and the products formed during the chlorination reaction. Solvents are examples of external compounds. Secondly, such a recycling stream allows reducing the purge flow from the reactor, and therefore a reduction in the size of the installations for treating the purges. All these advantages contribute to a reduction in the overall cost of the process.

The expression "liquid stream that supplies the chlorination reactor" is understood to mean any stream of material that is liquid at the temperature for introduction into the reactor, and which is introduced into the reactor. These liquid streams may contain various compounds such as, for example, glycerol, monochloropropanediol and the chlorinating agent, impurities present in the glycerol, monochloropropanediol and chlorinating agent, an organic solvent, water, a catalyst for the reaction, reaction intermediates and products and by-products of the reaction.

The expression "liquid recycling stream" is understood to mean any stream of material derived from at least one step of the dichloropropanol manufacturing process located downstream of the reactor, which is liquid at the temperature for introduction into the reactor, and which is introduced into the reactor.

This step of the process downstream of the reactor may be a physical or chemical treatment step. Among the physical treatment steps, mention may, for example, be made of the operations for separation via stripping, distillation, evaporation, extraction, settling, centrifugation, precipitation, filtration and adsorption. Among the chemical treatment steps, mention may, for example, be made of a hydrolysis treatment intended to recover an optional catalyst and a transesterification treatment intended to recover the dichloropropanol and the catalyst.

The removal of water from the reaction medium via distillation of an azeotropic water/dichloropropanol mixture is an example of a physical treatment step downstream of the reactor. The liquid return stream of the distillation column is considered to be a recycling stream. The distillation system may be located on top of the chlorination reactor or in an external circulation loop of the reaction mixture.

In the process according to the invention, the liquid recycling stream forms at least 10 wt % of all the liquid streams introduced into the reactor, preferably at least 20 wt %, more preferably at least 50 wt %, even more preferably at least 90 wt % and most particularly preferably at least 95 wt %. The recycling stream forms at most 99 wt % of all the liquid streams introduced into the reactor, and particularly preferably at most 97.5%.

The process according to the invention may be carried out in batch, semi-continuous or continuous mode. Continuous mode is preferred.

In the process according to the invention, the liquid recycling stream generally comprises at least one of the following compounds: glycerol, monochloropropanediol, the chlorinating agent, a carboxylic acid, a carboxylic acid salt, an inorganic salt, a glycerol ester, a polyester of glycerol, a monochloropropanediol ester, a poly ester of monochloropropanediol, water, a catalyst, a solvent, dichloropropanol, a dichloropropanol ester, a glycerol oligomer, a partially chlorinated and/or esterified glycerol oligomer.

In the process according to the invention, the liquid recycling stream generally comprises from 0.01 to 25 wt % of glycerol, preferably from 0.1 to 20 wt %, more preferably from 0.2 to 15 wt % and most particularly preferably from 0.3 to 10 wt %.

In the process according to the invention, the liquid recycling stream generally comprises from 0.01 to 40 wt % of glycerol esters, preferably from 0.05 to 30 wt %, more preferably from 0.1 to 20 wt % and most particularly preferably from 0.2 to 15 wt %.

In the process according to the invention, the liquid recycling stream generally comprises from 0.1 to 70 wt % of monochloropropanediol, preferably from 0.5 to 60 wt %, more preferably from 1 to 50 wt % and most particularly preferably from 6 to 49 wt %.

In the process according to the invention, the liquid recycling stream generally comprises from 5 to 90 wt % of monochloropropanediol esters, preferably from 10 to 85 wt %, more preferably from 20 to 82 wt % and most particularly preferably from 25 to 80 wt %.

In the process according to the invention, the liquid recycling stream generally comprises from 0.1 to 60 wt % of partially chlorinated and/or esterified glycerol oligomers, preferably from 0.2 to 50 wt %, more preferably from 1 to 45 wt % and most particularly preferably from 2 to 40 wt %.

The glycerol in the process according to the invention may be obtained starting from fossil raw materials or starting from renewable raw materials, preferably starting from renewable raw materials.

The expression "fossil raw materials" is understood to mean materials derived from the treatment of petrochemical natural resources, for example oil, natural gas and coal. Among these materials, organic compounds that consist of a number of carbon atoms which is a multiple of 3 are preferred. Allyl chloride, allyl alcohol and "synthetic" glycerol are particularly preferred. The term "synthetic" glycerol is understood to mean a glycerol generally obtained from petrochemical resources.

The expression "renewable raw materials" is understood to mean materials derived from the treatment of renewable natural resources. Among these materials, "natural" glycerol is preferred. "Natural" glycerol may, for example, be obtained by conversion of sugars via thermochemical processes, these sugars possibly being obtained starting from biomass, as described in "Industrial Bioproducts: Today and Tomorrow, Energetics, Incorporated for the U.S. Department of Energy, Office of Energy Efficiency and Renewable Energy, Office of the Biomass Program, July 2003, pages 49, 52 to 56". One of these processes is, for example, catalytic hydrogenolysis of sorbitol obtained by thermochemical conversion of glucose. Another process is, for example, catalytic hydrogenolysis of xylitol obtained by hydrogenation of xylose. Xylose may, for example, be obtained by hydrolysis of hemicellulose contained in maize fibres. The expressions "natural glycerol" or "glycerol obtained from renewable raw materials" are understood to mean, in particular, glycerol obtained during the manufacture of biodiesel or else glycerol obtained during conversions of fats or oils of vegetable or animal origin, in general such as saponification, transesterification or hydrolysis reactions.

Among the oils that can be used to manufacture natural glycerol, mention may be made of all common oils, such as palm, palm kernel, coconut, babassu, old or new rapeseed, sunflower, maize, castor and cottonseed oils, arachis, soybean, linseed and sea kale oils and all the oils derived from, for example, sunflower or rapeseed plants obtained by genetic modification or hybridization.

Use can even be made of used frying oils, various animal oils, such as fish oils, tallow, lard and even abattoir fats.

Among the oils used, mention may also be made of oils partially modified, for example, by polymerization or oligomerization such as, for example, the "stand oils" of linseed and sunflower oils and blown vegetable oils.

A particularly suitable glycerol may be obtained during the conversion of animal fats. Another particularly suitable glycerol may be obtained during the manufacture of biodiesel. Another particularly suitable glycerol may be obtained during the fatty acid manufacture.

In one embodiment of the process according to the invention, a glycerol external to the process according to the invention is used. The term "external" glycerol is understood to mean glycerol which is not recycled in the process according to the invention.

In another embodiment of the process according to the invention, a mixture of glycerol "external" to the process according to the invention and of glycerol "internal" to the process according to the invention is used. The term "internal" glycerol is understood to mean glycerol which has been separated from the reaction products formed in the process according to the invention and which has then been recycled in the process according to the invention.

The monochloropropanediol used in the process according to the invention may be obtained by any route, for example by reaction between glycerol and the chlorinating agent or by hydrolysis of epichlorohydrin.

In a first embodiment variant of the process according to the invention, a monochloropropanediol extrinsic to the process according to the invention is used. The term "extrinsic" monochloropropanediol is understood to mean monochloropropanediol which is not one of the products formed in the process according to the invention.

In a second embodiment variant of the process according to the invention, which is preferred, a monochloropropanediol intrinsic to the process according to the invention is used. The term "intrinsic" monochloropropanediol is understood to mean monochloropropanediol which is one of the products formed in the process according to the invention, which has been separated from the other reaction products and which has then been recycled in the process according to the invention.

In the process according to the invention, the sum of the glycerol and monochloropropanediol contents in all the liquid streams introduced into the reactor is preferably less than or equal to 49 wt %, more preferably less than or equal to 45 wt % and most particularly preferably less than or equal to 40 wt %. This content is generally greater than 1 wt %.

In the process according to the invention, the glycerol content in all the liquid streams introduced into the reactor is preferably less than or equal to 49 wt %, more preferably less than or equal to 30 wt % and most particularly preferably less than or equal to 20 wt %. This content is generally greater than 1 wt %.

When the glycerol and monochloropropanediol are present in all the liquid streams introduced into the reactor, the glycerol content in the mixture of glycerol and monochloropropanediol is generally greater than or equal to 1 wt %, usually greater than or equal to 5 wt %. This content is generally less than or equal to 99.9 wt %, usually less than or equal to 90 wt %.

In the process according to the invention, the chlorinating agent generally comprises hydrogen chloride. The hydrogen chloride may be gaseous hydrogen chloride, an aqueous solution of hydrogen chloride or a mixture of the two, preferably gaseous hydrogen chloride or a mixture of gaseous hydrogen chloride and an aqueous solution of hydrogen chloride.

In the process according to the invention, the reaction between glycerol and/or the chlorinating agent may be carried out in the presence of a catalyst, preferably a carboxylic acid or a carboxylic acid derivative, and most particularly preferably adipic acid or an adipic acid derivative. The expression "carboxylic acid derivatives" is understood to mean carboxylic acid halides, carboxylic acid esters, carboxylic acid anhydrides, carboxylic acid amides and mixtures of at least two of them.

In the process according to the invention, it is possible to use an organic solvent, such as a chlorinated organic solvent, an alcohol, a ketone, an ester or an ether, a non-aqueous solvent that is miscible with glycerol and/or chloropropanediol such as dioxane, phenol, cresol and dichloropropanol, or heavy products from the reaction, such as glycerol oligomers that are at least partially chlorinated and/or esterified.

In the process for manufacturing dichloropropanol according to the invention, the reaction between glycerol and/or chloropropanediol, and the chlorinating agent is preferably carried out in a liquid reaction medium. The liquid reaction medium may be single phase or multiphase.

The liquid reaction medium is formed by all the solid, liquid or gaseous compounds dissolved or dispersed at the reaction temperature.

The reaction medium generally comprises the reactants, catalyst, solvent, impurities present in the reactants, in the solvent and in the catalyst, reaction intermediates and products and by-products of the reaction.

The term "reactants" is understood to mean glycerol and/or monochloropropanediol, and the chlorinating agent. The monochloropropanediol may be 3-chloro-1,2-propanediol or 2-chloro-1,3-propanediol or a mixture of these two isomers.

Among the impurities present in the glycerol, mention may be made of carboxylic acids, carboxylic acid salts, of fatty acids esters such as mono-, di- and triglycerides, fatty acids esters with alcohols used during transesterification, inorganic salts such as alkali and alkaline-earth metal chlorides and sulphates.

Among the reaction intermediates, mention may be made of monochloropropanediol and its esters and/or polyesters, esters and/or polyesters of glycerol and dichloropropanol esters.

The glycerol ester may therefore be, depending on the case, an impurity of the glycerol or a reaction intermediate.

The monochloropropanediol may be, depending on the case, a reactant or a reaction intermediate.

The expression "products of the reaction" is understood to mean dichloropropanol and water.

The dichloropropanediol may be 1,3-dichloro-2-propanol or 2,3-dichloro-1-propanol or a mixture of these two isomers.

The water may be water formed in the chlorination reaction and/or water introduced into the process, for example via the glycerol and/or the chlorinating agent.

Among the by-products, mention may be made, for example, of partially chlorinated and/or esterified glycerol oligomers.

The reaction intermediates and the by-products may be formed in the various steps of the process, such as for example, during the dichloropropanol manufacturing step and during the steps for separating the dichloropropanol.

In the process according to the invention, when the reactor is supplied by a liquid stream, this stream comprises the streams of reactants, catalyst, solvent and the recycling stream or streams.

In the process according to the invention, when the reactor is supplied by several liquid streams, these streams comprise the streams of reactants, catalyst and solvent, and recycling streams and mixtures thereof, and one of the streams is composed solely of a recycling stream.

In the process according to the invention, the reaction between glycerol and/or monochloropropanediol and the chlorinating agent is carried out at a temperature generally greater than or equal to 70° C., preferably greater than or equal to 90° C. and most particularly preferably greater than or equal to 110° C. This reaction temperature is generally less than or equal to 160° C., preferably less than or equal to 150° C. and most particularly preferably less than or equal to 140° C.

In the process according to the invention, the reaction between glycerol and/or monochloropropanediol and the chlorinating agent is carried out at a partial pressure of hydrogen chloride generally greater than or equal to 0.002 bar, preferably greater than or equal to 0.02 bar and most particularly preferably greater than or equal to 0.05 bar. This pressure is generally less than or equal to 50 bar, preferably less than or equal to 30 bar and most particularly preferably less than or equal to 20 bar.

In one embodiment of the process according to the invention, the content of hydrogen chloride in the liquid reaction medium relative to the sum of the water and hydrogen chloride contents in the liquid reaction medium is generally less than or equal to 20 wt %, preferably less than or equal to 17 wt % and more particularly preferably less than or equal to 15 wt %.

In another embodiment of the process according to the invention, the content of hydrogen chloride in the liquid reaction medium relative to the sum of the water and hydrogen chloride contents in the liquid reaction medium is generally greater than or equal to 20 wt %, preferably greater than or equal to 30 wt % and more particularly preferably greater than or equal to 40 wt %.

The invention also relates to a process for manufacturing epichlorohydrin comprising the process for manufacturing dichloropropanol followed by a process for the dehydrochlorination of dichloropropanol.

The epichlorohydrin obtained by dehydrochlorination of dichloropropanol may be used in the manufacture of epoxy resins.

The invention finally relates to a process for manufacturing epoxy resins, in which epichlorohydrin, at least one part of which was obtained in the process for manufacturing epichlorohydrin according to the invention, is subjected to a reaction with at least one compound containing at least two active hydrogen atoms. These compounds comprise polyphenols, monoamines and diamines, aminophenols, heterocyclic imides and amides, diols including ethylene glycol and propylene glycol and aliphatic polyols, and fatty acid dimers. In the process for manufacturing epoxy resins, another part of the epichlorohydrin may be obtained by a process other than the dehydrochlorination of dichloropropanol derived from the chlorination of glycerol, such as a process for dehydrochlorination of dichloropropanol derived from hypochlorination of allyl chloride, a process for dehydrochlorination of dichloropropanol derived from chlorination of allyl alcohol, or an allyl chloride epoxidation process.

The epoxy resins thus obtained may be used in coating applications and in structural applications. The coating applications relate to the fields of maritime transport and of industrial maintenance (anticorrosion primer paints for metal and concrete structures), of coatings for metallic containers (food preserves, cans for drinks, drums, buckets and aerosol bottles) and for windings, of motor vehicle coatings (primers), of inks and masks for electronic circuits. The structural applications relate to the fields of structural composites (epoxy resin composites with glass, boron, carbon and aromatic polyamide fibres), of civil engineering, of floor covering (paints for coating floors, parquet, paving, tiling, self-levelling coatings, roughcast floors, tempered floors, floor coverings for cold rooms), of construction, of electrical equipment (sealing of electrical and electromechanical devices such as battery housings, resistors, fuses, thermal circuit breakers, cable joints, windings) and of electronic equipment (coatings and laminated sheets for printed circuits and encapsulation of printed circuits), of adhesives (bonding of different materials such as metals, glass, ceramics, wood, concrete, plastics) and of tooling (prototypes, master patterns, moulds and other parts) for the aerospace, automotive, foundry and maritime construction industries.

Epoxy resins also find applications in the fields of energy (wind energy), of aeronautics (honeycomb sandwich panels, helicopter rotor blades, cowls and engine nacelles, flaps, ailerons, rudders) and of fluid (gas, oil) transport.

The example below is intended to illustrate the invention without, however, limiting it.

EXAMPLE 1

According to the Invention

FIG. 1 represents one particular scheme of an installation which has been used to apply the dichloropropanol production process according to the invention.

A reactor (4) was continuously supplied, at 130° C. and at atmospheric pressure, with glycerol via the line (1) and a 34 wt % aqueous solution of hydrogen chloride via the line (2). A distillation column (6) was supplied via the line (5) with a gas phase produced by the reactor (4); the residue from the column (6) was recycled via the line (8) to the reactor (4). The production stream (7) contains most of the water produced by the process and a first part of the dichloropropanol production. A liquid purge was drawn off from the reactor (4) via the line (9) and supplied an evaporator (10) where an operation of partial evaporation of the mixture was carried out by heating; the gas phase which contains most of the hydrogen chloride and the water from the stream (9) was recycled via the line (11) to the bottom of the column (6). A stripping column (13) was supplied by the liquid phase coming from the evaporator (10) via the line (12) and by a stream of nitrogen introduced via the line (16); a second part of the dichloropropanol production was collected at the top of the column (13) via the line (14) and the residue from the column (13) was recycled to the reactor (4) via the line (15). A purge of the reaction mixture from the reactor (4), in which the heavy by-products of the reaction, such as chlorinated glycerol oligomers, accumulated, was carried out in batch mode via the line (17). The amount of catalyst removed from the reactor via the purge was compensated for by an addition of catalyst via the line (3). The weight proportions of glycerol introduced into the reactor (4) via the lines (1) and (15) and of glycerol monochlorohydrin introduced via the line (15) were respectively equal to 3.9% and 14.1% of the total of the liquid streams supplying the reactor via the lines (1), (2), (8) and (15). The recycling stream which supplied the reactor (4) via the lines (8) and (15) was 90% of all of the liquid streams introduced into the reactor (4).

EXAMPLE 2

Not According to the Invention

Aqueous hydrochloric acid with a concentration of 4 mol of hydrogen chloride/kg of solution (96.8 g/h), glycerol (22 g/h) and caprylic acid (6.37 g/h) have been introduced at a constant flow rate into a 350 ml glass reactor thermostatted at a temperature of 120° C. The reactor, which functioned at atmospheric pressure, was equipped with an overflow system for maintaining a constant volume of liquid. The reaction mixture fraction that was vaporized was evacuated from the reactor and condensed at ambient temperature. The condensate separated into 2 phases: a dense organic phase containing mainly dichloropropanol and a lighter aqueous phase containing most of the hydrochloric acid which had not reacted. The liquid mixture collected at the overflow outlet contained the remainder of the dichloropropanol production. No flow was recycled to the reactor. The process was operated during 25 h to equilibration. The global dichloropropanol productivity estimated from the flows and the compositions of the condensate and the overflow outlet was 26.4 g dichloropropanol/h/l.

EXAMPLE 3

According to the Invention

Aqueous hydrochloric acid with a concentration of 4 mol of hydrogen chloride/kg of solution (98.7 g/h), glycerol (22 g/h) and caprylic acid (6.21 g/h) have been introduced at a constant flow rate into a 350 ml glass reactor thermostatted at a temperature of 119.4° C. The reactor, which functioned at atmospheric pressure, was equipped with an overflow system for maintaining a constant volume of liquid. The reactor was surmounted by a distillation column for rectifying the reaction medium fraction vaporized. The reflux to the column was adjusted so that a flow of 155 g/h of liquid was returned from the distillation column to the reactor. The mixture exiting the top of the distillation column was condensed at ambient temperature. The condensate separated into 2 phases: a dense organic phase containing mainly dichloropropanol and a lighter aqueous phase containing most of the hydrochloric acid which had not reacted. The liquid mixture collected at the overflow outlet contained the remainder of the dichloropropanol production. The global dichloropropanol productivity estimated from the flows and the compositions of the condensate and the overflow outlet after equilibration was 46 g dichloropropanol/h/l.

The invention claimed is:

1. A process for manufacturing dichloropropanol comprising a reaction between glycerol and/or monochloropropanediol and a chlorinating agent in a reactor which is supplied with one or more liquid streams, wherein the sum of the glycerol and monochloropropanediol contents in all the liquid streams introduced into the reactor is less than 50 wt %, and wherein all the liquid streams introduced into the reactor comprise at least one liquid recycling stream, the recycling stream forming at least 10 wt % of all the liquid streams introduced into the reactor.

2. The process according to claim 1, wherein the liquid recycling stream forms at least 20 wt % and at most 99 wt % of all the liquid streams introduced into the reactor.

3. The process according to claim 1, wherein the reactor is supplied in continuous mode.

4. The process according to claim 1, wherein the liquid recycling stream comprises at least one of the following compounds selected from the group consisting of glycerol, monochloropropanediol, the chlorinating agent, a salt, a glycerol ester, a monochloropropanediol ester, water, a catalyst, a solvent, dichloropropanol, a dichloropropanol ester, a glycerol oligomer, a chlorinated, and esterified glycerol oligomer.

5. The process according to claim 1, wherein the recycling stream contains from 0.01 to 25 wt % of glycerol.

6. The process according to claim 1, wherein the recycling stream contains from 0.1 to 70 wt % of monochloropropanediol.

7. The process according to claim 1, wherein the sum of the glycerol and monochloropropanediol contents in all the liquid streams introduced into the reactor is less than or equal to 40 wt %.

8. The process according to claim 1, wherein the glycerol is obtained starting from renewable raw materials and wherein the chlorinating agent contains gaseous hydrogen chloride or a mixture of gaseous hydrogen chloride and an aqueous solution of hydrogen chloride.

9. The process according to claim 1, which is followed by dehydrochlorination of the dichloropropanol manufactured by said process to manufacture epichlorohydrin.

10. The process according to claim 9, wherein the epichlorohydrin is utilized in the manufacture of epoxy resins.

* * * * *